(12) United States Patent
Dhuper et al.

(10) Patent No.: US 7,360,541 B2
(45) Date of Patent: Apr. 22, 2008

(54) ENDOTRACHEAL TUBE WITH AEROSOL DELIVERY FEATURE

(76) Inventors: Sunil Kumar Dhuper, 47 Red Ground Rd., Old Westbury, NY (US) 11568; Sarita Dhuper, 47 Red Ground Rd., Old Westbury, NY (US) 11568

( * ) Notice: Subject to any disclaimer, the term of this patent is extended or adjusted under 35 U.S.C. 154(b) by 0 days.

(21) Appl. No.: 11/538,366

(22) Filed: Oct. 3, 2006

(65) Prior Publication Data

US 2007/0102000 A1    May 10, 2007

Related U.S. Application Data

(63) Continuation of application No. 10/162,740, filed on Jun. 6, 2002, now abandoned.

(51) Int. Cl.
*A61M 16/00* (2006.01)
*A61M 11/00* (2006.01)

(52) U.S. Cl. .................. 128/207.14; 128/200.23; 128/200.26; 128/203.15

(58) Field of Classification Search ........... 128/200.23, 128/200.24, 200.26, 202.27, 207.14, 207.15, 128/207.16, 203.15, 203.12, 203.13, 200.19, 128/200.11, 200.14; 239/390, 391, 392, 239/393, 394, 395, 396, 548, 54, 9, 553.5, 239/561, 562, 567; 604/96.01, 915, 102.02, 604/102.03
See application file for complete search history.

(56) References Cited

U.S. PATENT DOCUMENTS

| 335,175 | A |   | 2/1886 | Blathwayt |
|---|---|---|---|---|
| 4,554,916 | A | * | 11/1985 | Watt ................. 128/203.12 |
| 4,584,998 | A | * | 4/1986 | McGrail ............. 128/207.15 |
| 4,669,463 | A |   | 6/1987 | McConnell |
| 4,739,756 | A | * | 4/1988 | Horn ................. 128/207.14 |
| 4,821,714 | A |   | 4/1989 | Smelser |
| 4,850,371 | A | * | 7/1989 | Broadhurst et al. ..... 600/532 |
| 5,146,916 | A | * | 9/1992 | Catalani ............ 128/207.14 |
| 5,231,983 | A | * | 8/1993 | Matson et al. ..... 128/207.14 |
| 5,438,982 | A | * | 8/1995 | MacIntyre .......... 128/207.14 |
| 5,513,630 | A |   | 5/1996 | Century |
| 5,542,412 | A |   | 8/1996 | Century |
| 5,570,686 | A |   | 11/1996 | Century |
| 5,579,758 | A |   | 12/1996 | Century |
| 5,588,424 | A | * | 12/1996 | Insler et al. ........ 128/207.15 |
| 5,594,987 | A |   | 1/1997 | Century |
| 5,606,789 | A |   | 3/1997 | Century |
| 5,642,730 | A |   | 7/1997 | Baran |
| 5,964,223 | A | * | 10/1999 | Baran ................ 128/207.14 |
| 6,079,413 | A |   | 6/2000 | Baran |

* cited by examiner

*Primary Examiner*—Teena Mitchell
*Assistant Examiner*—Annette Dixon
(74) *Attorney, Agent, or Firm*—Darby & Darby P.C.

(57) ABSTRACT

An endotracheal tube for insertion into a patient's trachea includes a drug delivery feature and is formed of an elongated body having a proximal end for connection to a ventilator device and an opposing distal end with a bore formed therein and terminating in at least one ventilation opening. The tube also has at least one drug delivery conduit formed in the elongated body and terminating at one end with a proximal opening and at an opposite end with a distal opening. The proximal opening is adapted to be fluidly connected to a drug delivery device adapter, wherein the at least one drug delivery conduit is separated from the bore along its entire length thereof from the proximal opening to the distal opening. The distal opening is formed at the distal end of the elongated body and is located closer to the distal end than the ventilation opening.

21 Claims, 14 Drawing Sheets

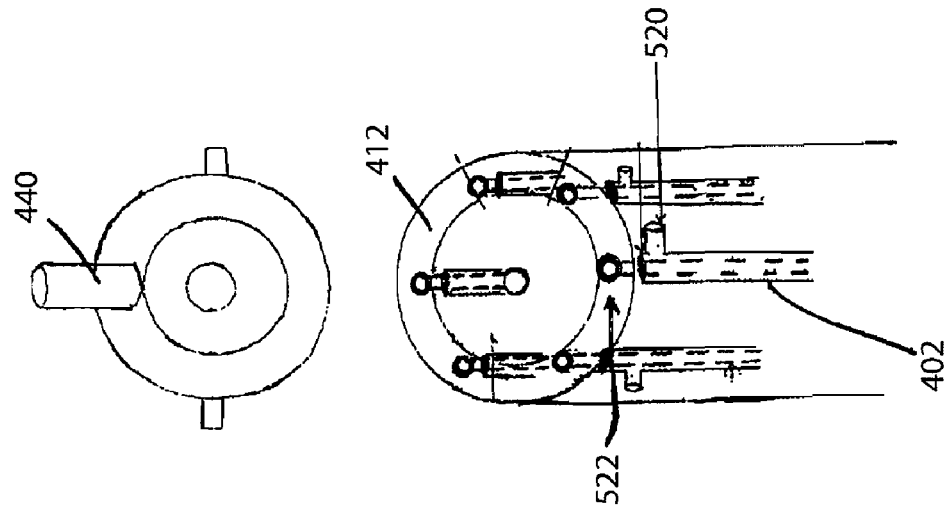
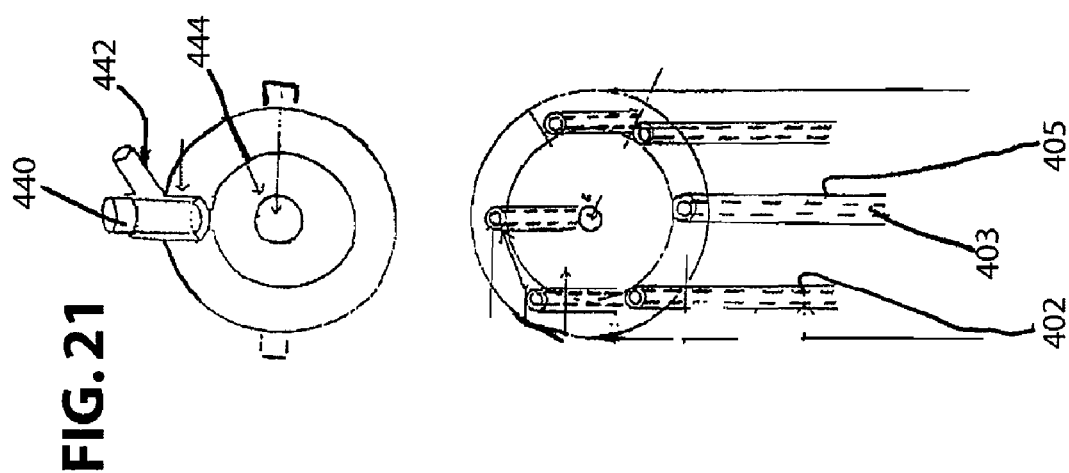
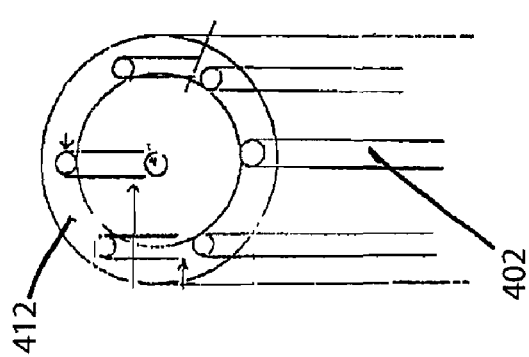

ENDOTRACHEAL TUBE WITH AEROSOL DELIVERY FEATURE

CROSS-REFERENCE TO RELATED APPLICATION

The present application is a continuation of U.S. patent application Ser. No. 10/162,740, filed Jun. 6, 2002 now abandoned, which is hereby incorporated by reference in its entirety.

TECHNICAL FIELD

The present invention relates to medical-surgical devices for intubation, i.e., endotracheal tube (ETT), intended for tracheal insertion in patients requiring mechanical ventilation. This tube is specifically designed for improved intrapulmonary deposition of aerosol particles, both quantitatively, as well as qualitatively in patients on mechanical ventilation via endotracheal tube. Multiple medications readily lend themselves for pulmonary administration. Many diagnostic and therapeutic agents that can be utilized through this route are the bronchodilators, anti-inflammatory agents like steroids, antibiotics, anticholinergics, heparin, surfactant, antiproteases, gene transfer products, insulin, radioactive dyes, etc.

BACKGROUND

The advantages of intrapulmonary drug delivery as opposed systemic administration are well known. The desired effect at the site of local delivery as opposed to systemic administration minimizes side effects and is the preferred methodology for delivery of several medications. Conventional methods for aerosol delivery have resulted in failure of effective drug delivery to the lungs. They are limited not only in total dose delivery but have also failed to achieve uniform intrapulmonary drug distribution. The two methods currently available for intrapulmonary drug delivery are highly inefficient. They are: (I) Liquid bolus: The medication is instilled in the form of liquid bolus via a bronchoscope or through an ETT. The distribution by this method is non-uniform. Also there is a significant risk of inducing respiratory distress and hypoxemia. (II) Aerosol Inhalation: Conventional methods of aerosol drug delivery have employed Metered Dose Inhalers (MDI's) with low boiling point propellants (CFC, HFA) or aerosol particles generated by heat, traditional compressed air nebulizers, or ultrasonic nebulizers. Even though these methods produce aerosol particles in respirable range (<5 microns) compared with the liquid bolus medication, they are limited in total dose delivery and lack uniform distribution of medication to the lungs. Only a small fraction of the medication reaches the lungs as the majority of the aerosol particles either adhere to the nasal passages and oropharynx or are exhaled out. Efficiency of aerosol delivery drops even further in patients who are intubated and require mechanical ventilation. Inhalation of nebulized material through an endotracheal tube can generally result in deposition of only 1.87% of the delivered particles to the lungs. Methods have been employed that have a combined ventilator dispenser and adapter or other spacer devices with MDI's have revealed equally poor results as most of the aerosol particles adhere to the ETT, the connectors and the inspiratory limb of the corrugated plastic tube.

Investigators over the years have designed numerous endotracheal tubes in an attempt to overcome the hurdles associated with conventional methods of drug delivery to the respiratory system in patients on mechanical ventilation. Most designs of endotracheal tubes so far have only addressed the issue of drug delivery in the form of liquid bolus by incorporating drug irrigation devices in the traditional ETT in the form of secondary canalization with multiple micrometric openings.

Factors that influence uniform delivery of aerosol particles in the tracheobronchial tree are the mid-mean diameter of aerosol particles (which should be in the respirable range, i.e. <5 microns), velocity of the aerosol plume, geometry of the aerosol plume (narrow vs. wide), site of the plume generation (proximal, distal or in the lumen of the ETT), orientation of the plume (central vs. eccentric), time of actuation of MDI in the respiratory cycle, temperature and humidity in the respiratory circuit, etc. These features have not been addressed by any of the currently available endotracheal tubes incorporating drug irrigation devices.

U.S. Pat. No. 4,584,998 describes an ETT with up to three secondary lumens in addition to the primary lumen in which one lumen can serve the purpose of delivering atomized gases to the patient.

U.S. Pat. No. 4,669,463 shows ETT with a secondary lumen in the wall of the main lumen to deliver liquid medication to the respiratory system.

U.S. Pat. No. 4,821,714 describes an ETT with a secondary lumen to deliver medication to the respiratory system. The second lumen splits into two branches that terminate as two orifices, one at the distal tip and other along the exterior wall of the ETT.

Other commercial products include an ETT with a secondary lumen in the wall of the ETT that terminates at a perforation (Murphy eye). The single stream of medication splits when it impacts on the distal edge of the opening resulting in delivery of medication both internally and externally of the ETT.

U.S. Pat. No. 5,642,730 and U.S. Pat. No. 6,079,413 each describes a catheter system for delivery of aerosolized medicine for use with pressurized propellant canister. The system includes an extension catheter that has a length such that the proximal end is connected to the canister and the distal end is positioned in the primary lumen or secondary lumen of the ETT beyond its distal end in the respiratory system. The system describes an extremely complex methodology for centering the device, attenuating the whipping effect and for preventing impaction losses, especially carinal impaction. Over and above this system is too expensive for clinical utility and is only being used as an experimental tool in research laboratories.

U.S. Pat. No. 5,964,223 describes a nebulizing catheter system similar to U.S. Pat. No. 5,642,730. This system describes the flow of liquid medication through the lumen of a catheter which is nebulized at its tip by a flow of pressurized gas through a coaxial lumen.

In summary, none of the prior art ETT's provide means for effective local delivery of medication to the tracheobronchial tree of both lungs.

SUMMARY

The present invention relates to endotracheal tubes with an improved system of delivering aerosolized medication to patient's respiratory system. The main object of the present invention is to provide a modified ETT that serves the following purposes: (1) aerosol drug delivery to tracheobronchial tree; (2) generation and delivery of aerosol particles at the distal end of the ETT with mid mean diameter that will allow uniform distribution throughout the tracheobronchial tree; (3) generation and delivery of aerosol particles at the distal end of the ETT such that a significant fraction of the aerosol particles reach the tracheobronchial tree without adherence to the ETT; and (4) simple and inexpensive method of intrapulmonary drug delivery To achieve all the objects without interfering with the primary functions of the ETT. In other words, the present system does not impede intubation or in anyway make it more complicated for the operator, or more traumatic to the patient. The defined objects are obtained through the present invention, i.e., the ETT that incorporates several features. The present system uses a pressurized canister or a metered dose inhaler (MDI) to deliver aerosolized medication to the respiratory system. MDI is a system that uses a pressurized canister that contains either a suspension of pulverized particles of medication in a liquid propellant or a solution of the medication in a liquid propellant. When the canister is actuated, the mixture of medication and propellant is generated from the distal orifice or the nozzle of the canister.

In addition to the primary cannula for inflation of the distal balloon, the ETT can have six additional secondary cannulations (conduits). The secondary cannulations originate in the proximal half of the ETT and continue distally within the wall of ETT in six different tracts to terminate as six pinhole orifices at the distal tip of the ETT. The six orifices are arranged like the six edges of a hexagon, preferably at 1, 3, 5, 7, 9 and 11 o'clock positions (other arrangements are possible as well). The secondary cannulations exit the ETT in its proximal half and continue as six narrow tubular extensions outside the main frame of the ETT. The tubular extensions are preferably semi-flexible and terminate as six MDI adapters on the peripheral rim of the circular plate (again arranged like the six edges of a hexagon) or as cylindrical fittings for mating with MDI adapters. The terminal orifice of MDI or nozzle locks into the proximal port of MDI adapter. Actuation of MDI with this assembly would deliver medication at the distal tip of ETT.

The six flexible tubules are preferably further packaged in a single bigger hollow tube. The hollow tube along with six tubules terminate proximally on the under surface of a circular plate. The distal end of the hollow tube terminates on the outer wall of the ETT, the junction where six flexible tubules mate with six secondary cannulations. The circular plate has a connector in the center through which it attached to a second circular plate. The lower circular plate is fixed to the connector whereas the upper circular plate can freely rotate around the central connector. In the peripheral rim of the proximal circular plate is attached an MDI adapter. The MDI adapter tapers distally to terminate as an orifice that locks into the proximal orifice of the flexible tubule. The connector has a circular groove in the center and six grooves perpendicular to the circular groove equidistant from each other. These perpendicular grooves are in alignment (parallel) with the cylindrical fittings for MDI adapters. The upper circular plate can rotate around the circumference of the circular groove as well as move superiorly and inferiorly along the six perpendicular grooves. This arrangement permits the MDI adapter to move superiorly along the perpendicular groove of the central connector, which unlocks the MDI adapter from the flexible tubule and positions it in the circular groove. Rotation along the circular groove positions it in the next perpendicular groove. On caudal movement of the circular plate the MDI adapter can now lock into the second flexible tubule. Hence, similar repetitive movements permit the MDI adapter to lock into six flexible tubules one at a time in six different positions. Actuation of the MDI generates aerosol particles that would be propelled through the MDI adapter into flexible tubules, secondary cannulations and finally to be delivered at the terminal orifices at the tip of the ETT. The aerosolized particles generated at any given orifice will be preferentially delivered to one lung. However, six different aerosol plumes generated from six orifices in different positions would ensure a uniform distribution of aerosol particles to both lungs.

BRIEF DESCRIPTION OF THE DRAWING FIGURES

Further features of the present invention will become apparent in the accompanying drawings as well as the detailed description of the preferred embodiments.

Figure 1:
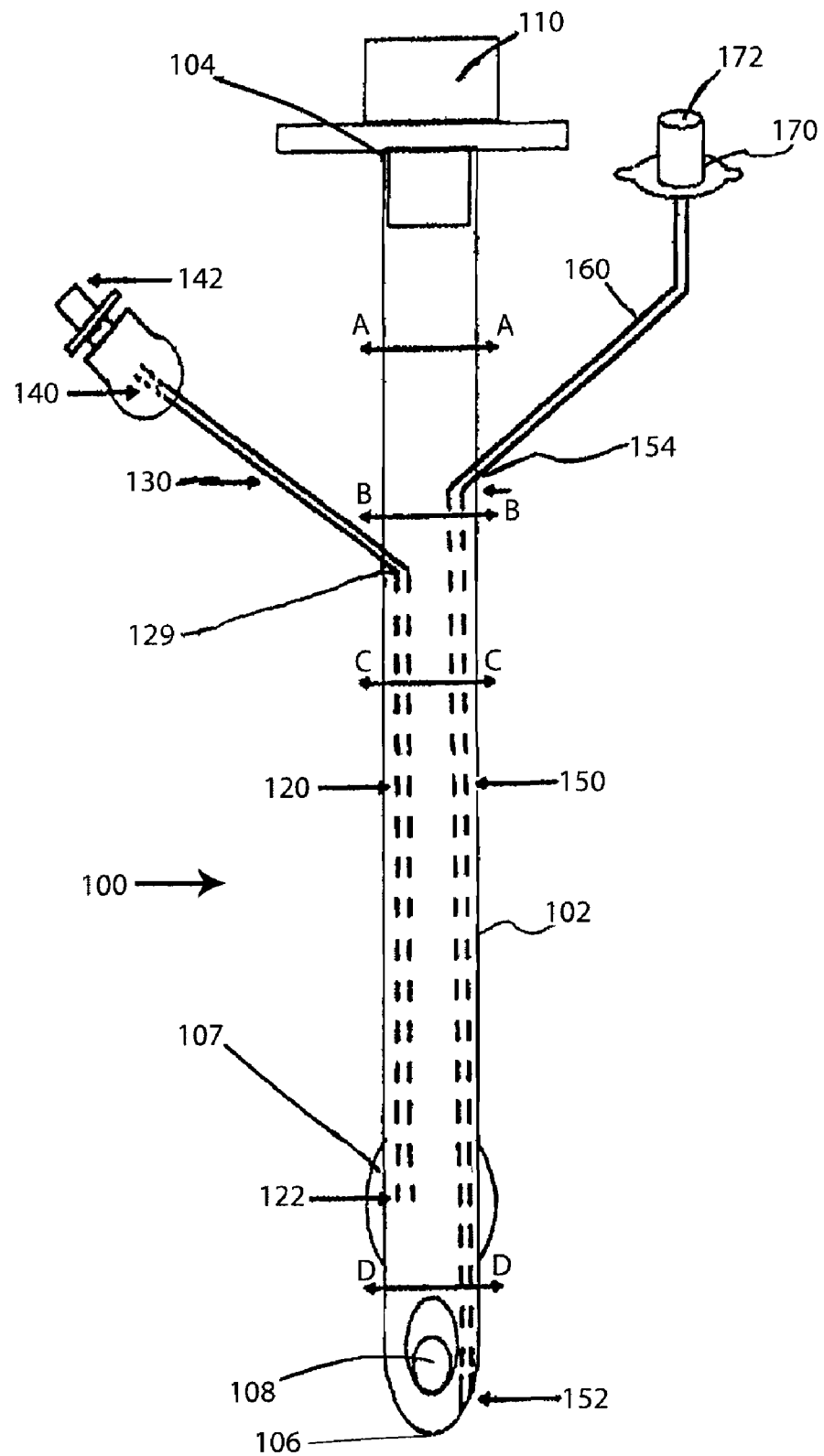
FIG. 1 is a side view of the longitudinal length of an ETT according to a first embodiment of the present invention.
Figure 2:
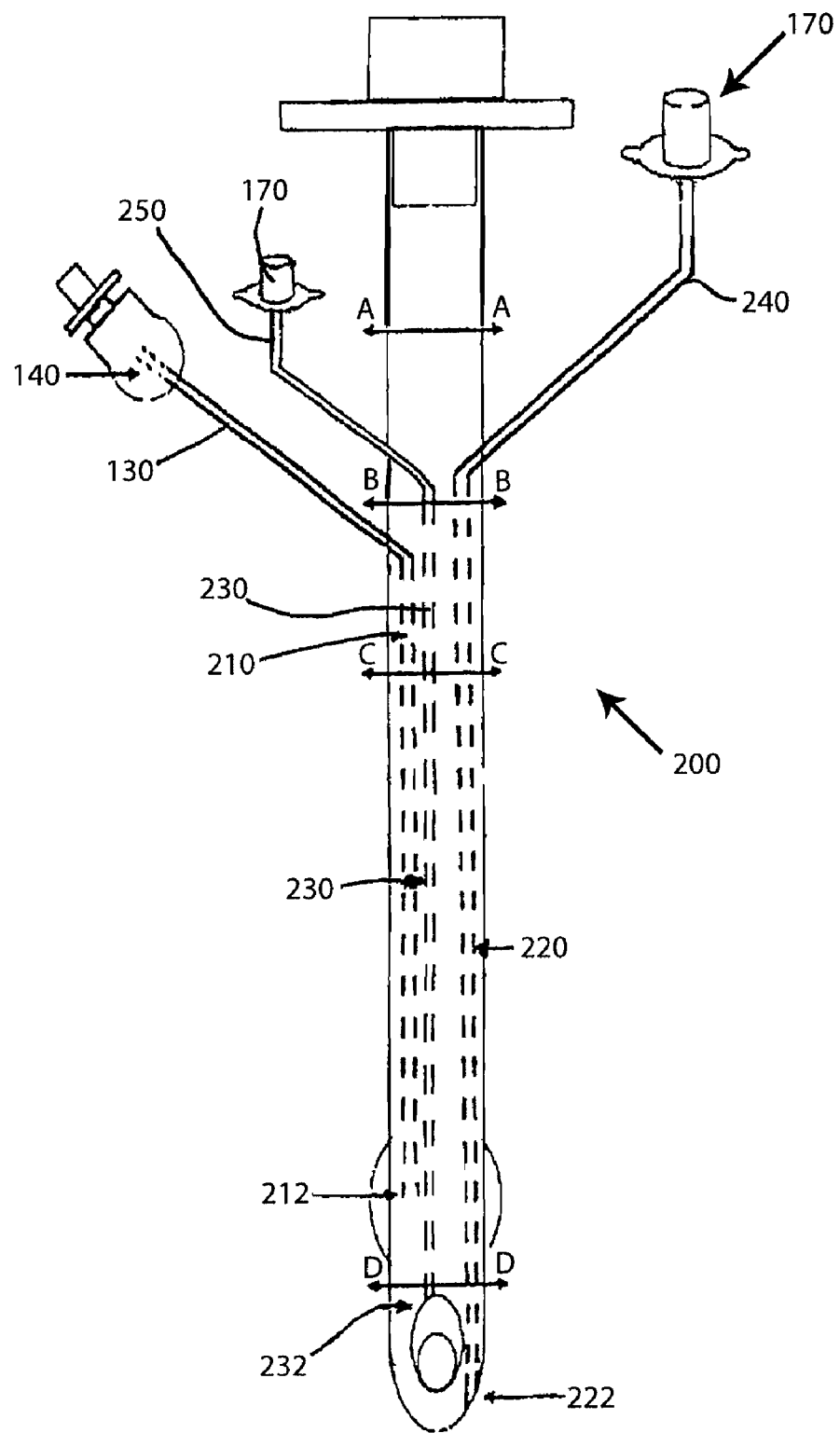
FIG. 2 is a side view of the longitudinal length of ETT according to a second embodiment of the present invention.
Figure 3:
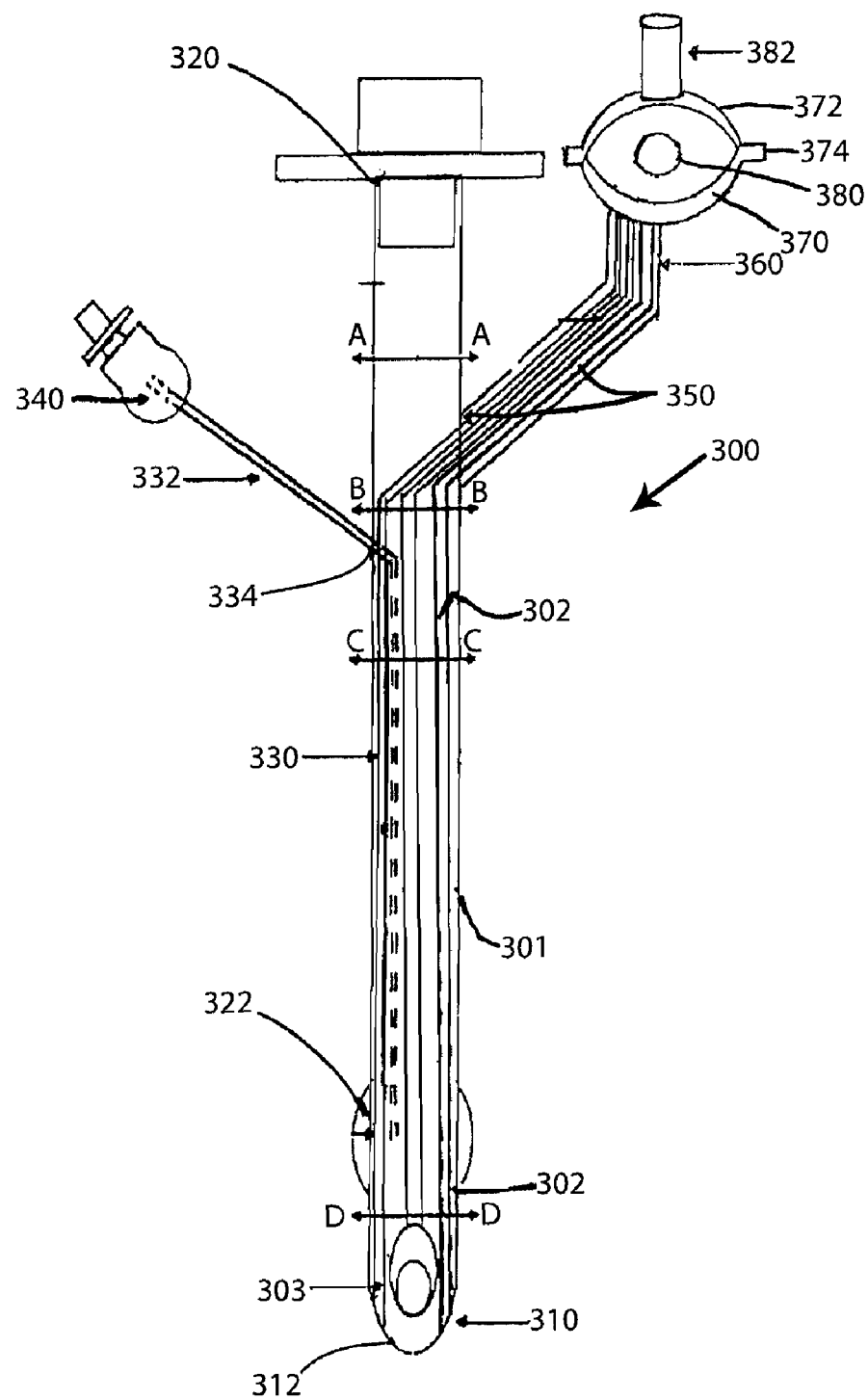
FIG. 3 is a side view of the longitudinal length of ETT according to a third embodiment of the present invention.
Figure 4:
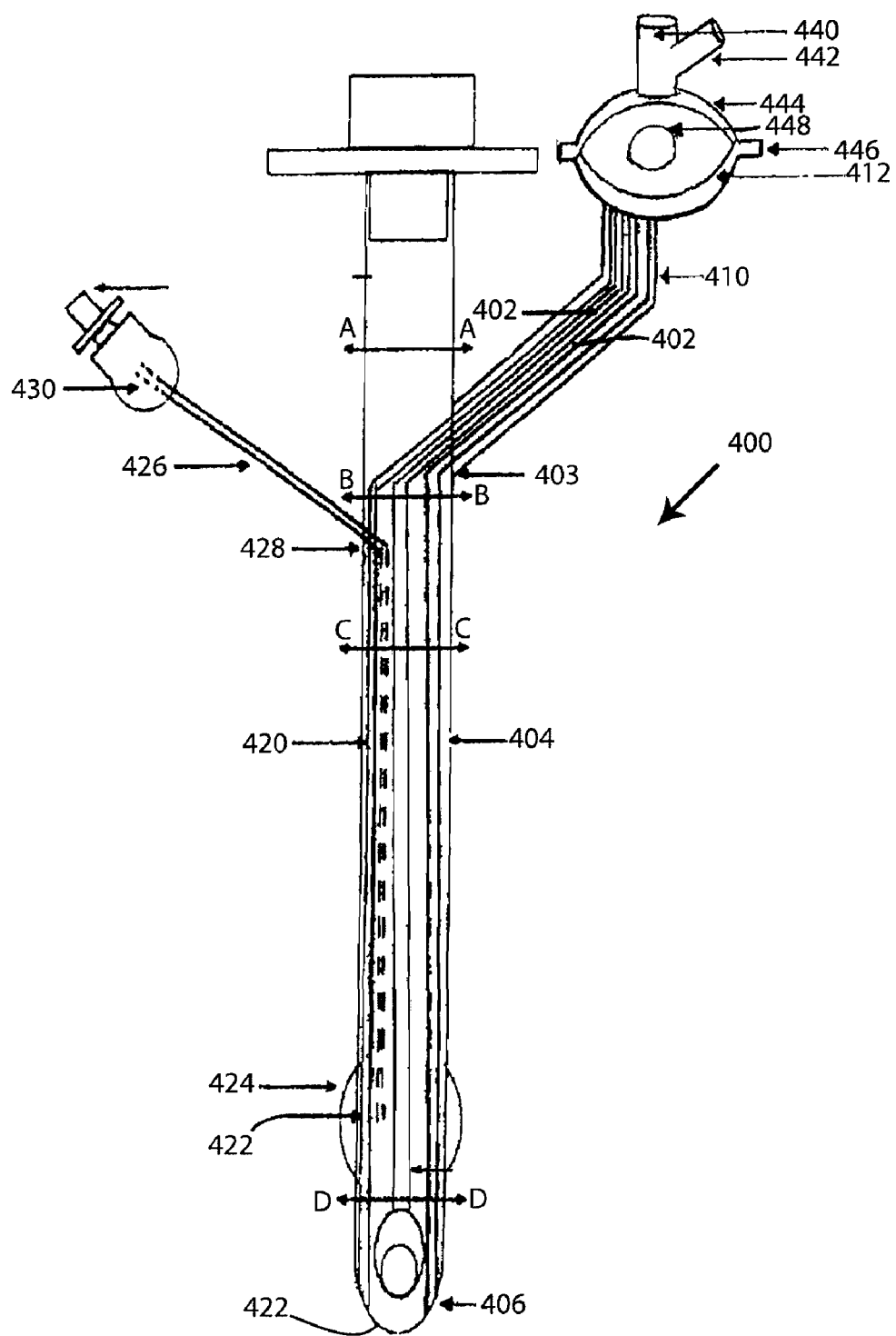
FIG. 4 is a side view of the longitudinal length of ETT according to a fourth embodiment of the present invention.
Figure 9A:
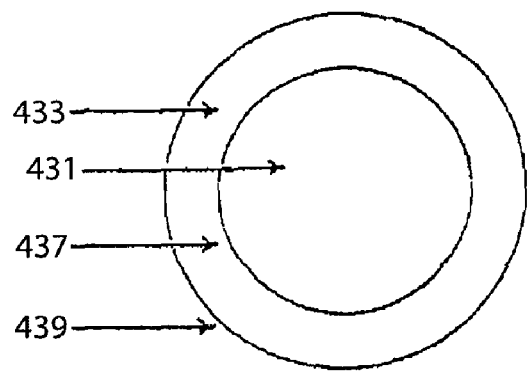
Figure 9B:
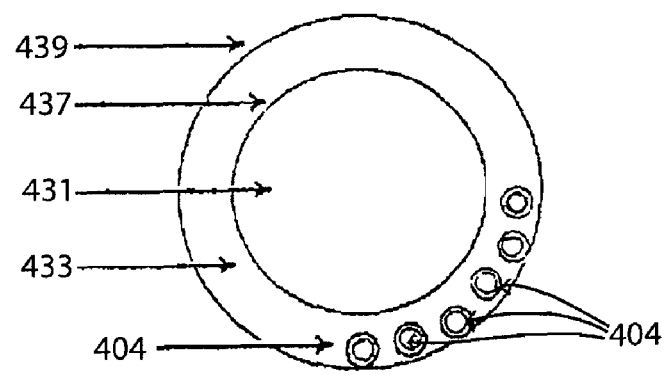
Figure 9C:
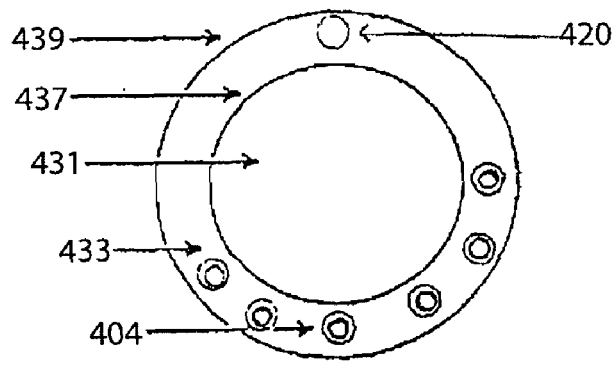
Figure 9D:
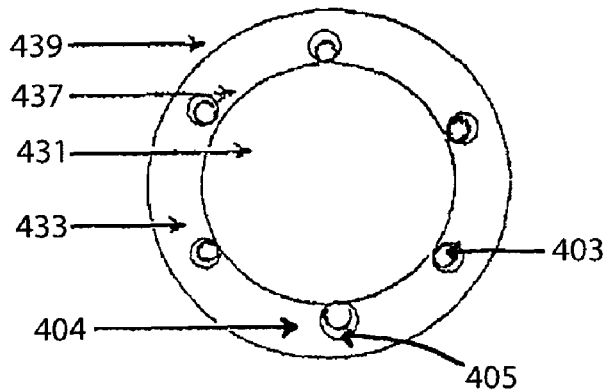
Figure 10:
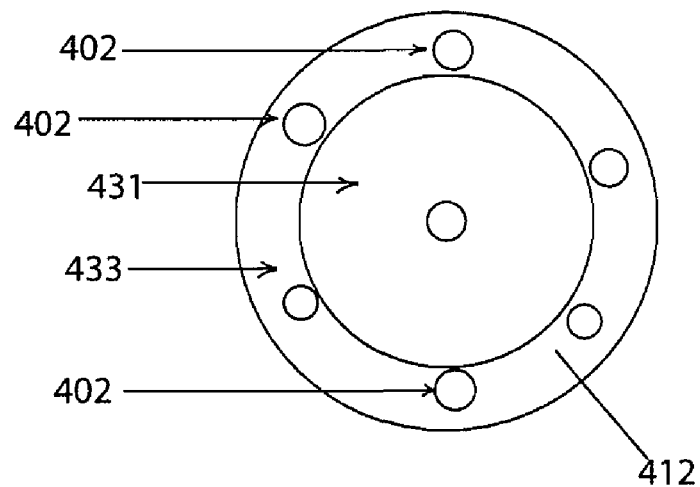
Figure 11:
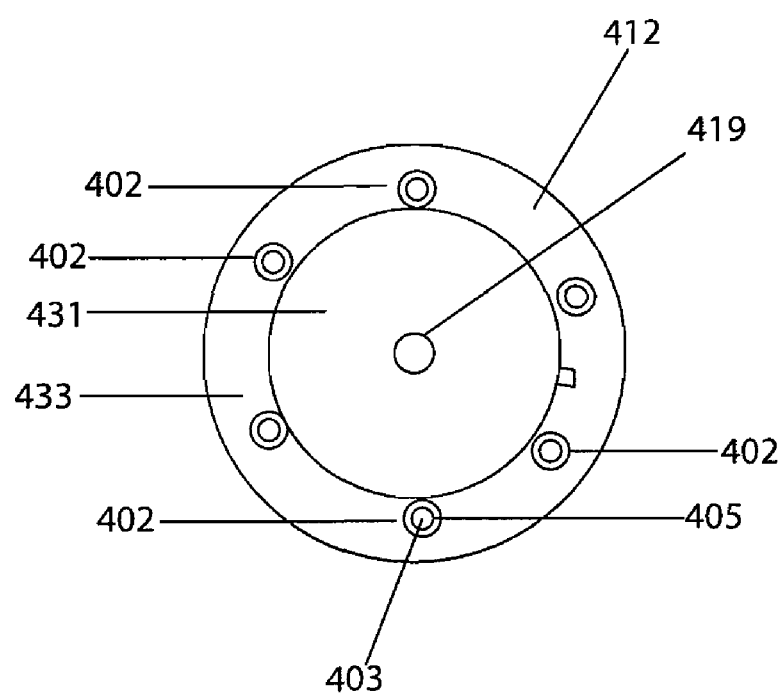
Figure 12:
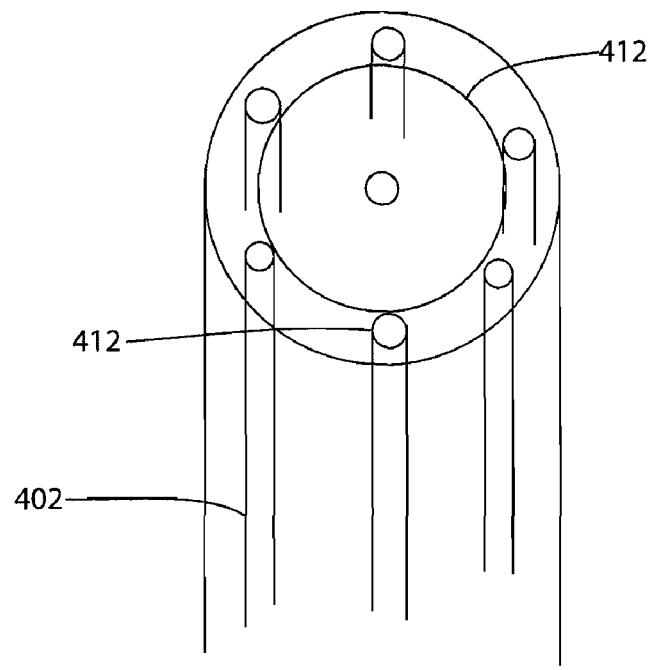
Figure 13:
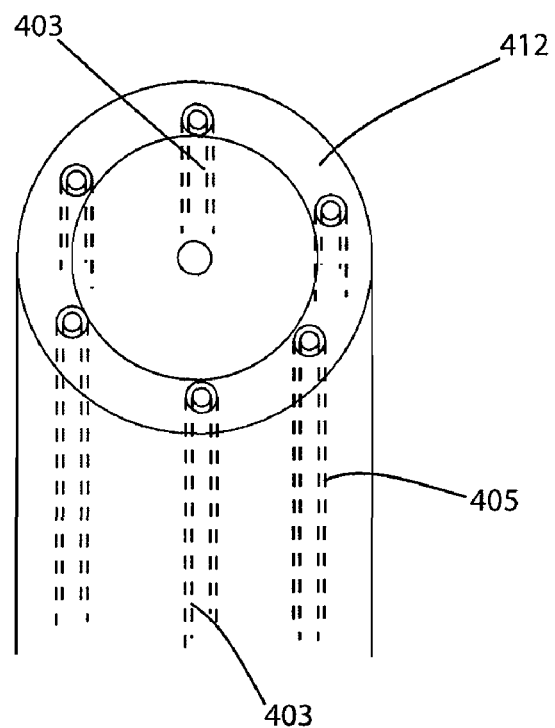
Figure 14:
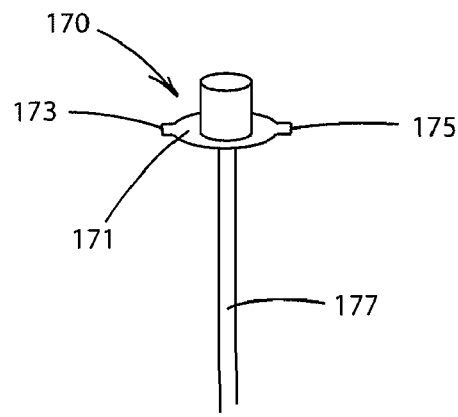
Figure 15:
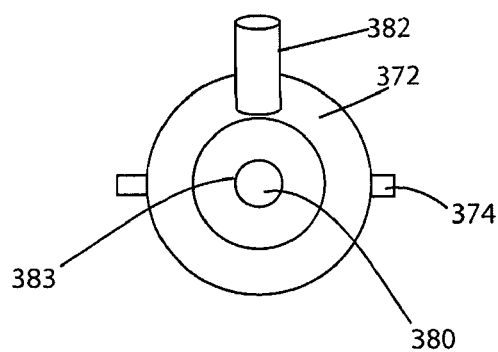
Figure 16:
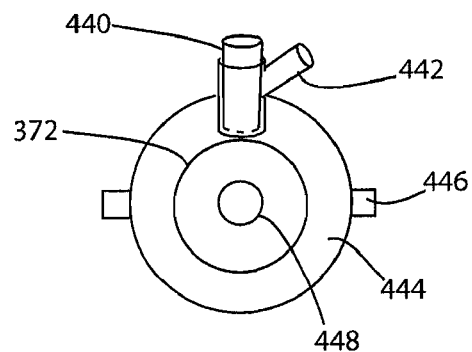
Figure 17:
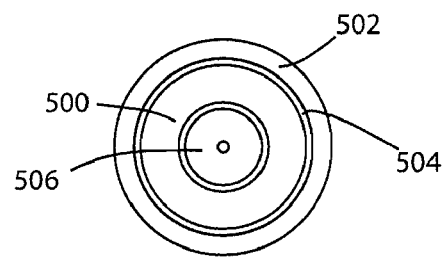
Figure 18:
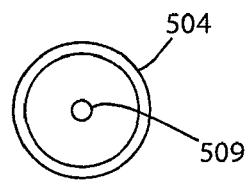
Figure 19:
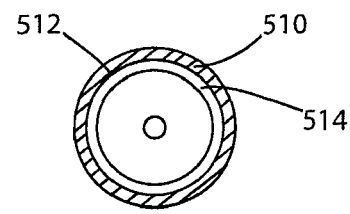
Figure 23:
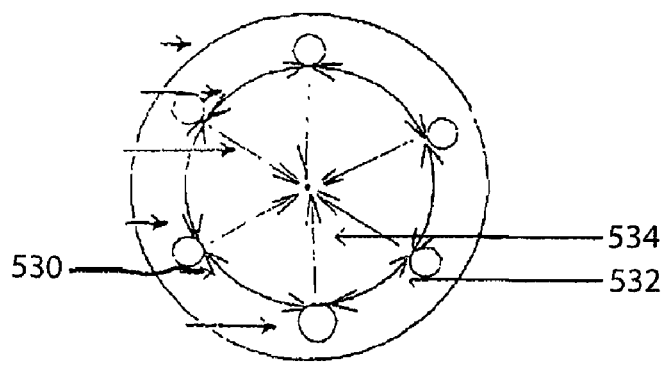
Figure 24:
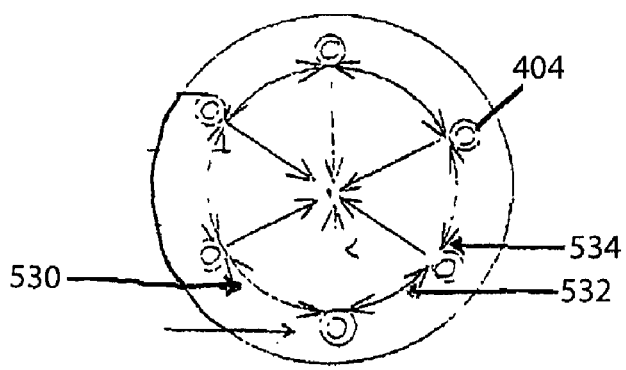
Figure 25:
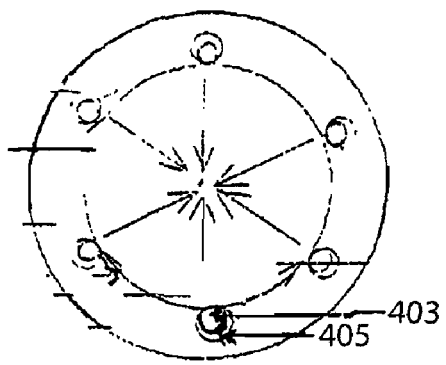

FIGS. 5a, 5b, 5c, and 5d, respectively, are expanded cross-sectional views of the endotracheal tube according to the present invention taken along sections a-a, b-b, c-c, and d-d of FIG. 1;

FIGS. 6a, 6b, 6c, 6d, respectively, are expanded cross-sectional views of the ETT according to the present invention taken along sections a-a, b-b, c-c, and d-d of FIG. 2;

FIGS. 7a, 7b, 7c, 7d, respectively, are expanded cross-sectional views of the ETT according to the present invention taken along sections a-a, b-b, c-c, and d-d of FIG. 3;

FIGS. 8a, 8b, 8c, 8d, respectively, are expanded cross-sectional views of the ETT according to the present invention taken along sections a-a, b-b, c-c, and d-d of FIG. 4;

FIGS. 9a, 9b, 9c, 9d, respectively, are expanded cross-sectional views of the ETT according to an alternative embodiment of the present invention taken along sections a-a, b-b, c-c, and d-d of FIG. 4;

FIG. 10 is an expanded cross-sectional view of a bottom circular plate of the ETT described in FIG. 3;

FIG. 11 is a cross-sectional view of a bottom circular plate of the ETT described in FIG. 4;

FIG. 12 is a perspective view of the bottom circular plate of the ETT described in FIG. 3;

FIG. 13 is a perspective view of the bottom circular plate of the ETT described in FIG. 4;

FIG. 14 is a perspective view of the top circular plate of the ETT described in FIGS. 1 and 2;

FIG. 15 is a perspective view of the top circular plate of the ETT described in FIG. 3;

FIG. 16 is a perspective view of the top circular plate of the ETT described in FIG. 4;

FIG. 17 is a cross-sectional view of the MDI adapter from above as described in FIGS. 14, 15 and 16;

FIG. 18 is a cross-sectional view of the MDI adapter from below as described in FIGS. 14 and 15;

FIG. 19 is a cross-sectional view of the adapter from the below as described in FIG. 16;

FIG. 20 is a perspective view of the upper and lower plates aligned together as described in FIGS. 3, 10 and 15;

FIG. 21 is a perspective view of the upper and lower plates aligned together as described in FIGS. 4, 11 and 16;

FIG. 22 is a perspective view of an alternative embodiment of the upper and lower plates aligned together as described in FIG. 21;

FIG. 23 is a view from above of the direction of the aerosol plume generated from the ETT as described in FIG. 3;

FIG. 24 is a view from above of the direction of the aerosol plume generated from the ETT as described in FIG. 4; and FIG. 25 is a view from above of the direction of the aerosol plume generated from the ETT as described in FIG. 4 with an alternative embodiment described in FIG. 9d.

DETAILED DESCRIPTION OF THE INVENTION

The present invention will now be described in detail by reference to the drawing figures, where as like parts as indicated by like reference numerals.

FIG. 1 shows a first embodiment of the present invention. FIG. 1 shows a longitudinal length of an ETT 100 which can be a conventional adult or pediatric ETT. The ETT 100 is an elongated hollow tube constructed from a plastic material (polymer) or silicone and is approximately 34 cm in the case of an adult ETT and smaller if for a pediatric application. The internal diameter of the tube 102 can vary from 2.5 mm to 10 mm and the external diameter can vary from 3.5 mm to 13 mm. The thickness of the wall of the tube 102 can vary from 0.5 mm to 2.0 mm. The tube 102 is a flexible elongated conduit with a concave surface on one side and a convex surface on the opposite side. A proximal end 104 is connected to an adapter 110 which enables it to be connected to an elongated tube of a mechanical ventilator (not shown). A distal end 106 has a 4 cm expandable cuff 107 starting approximately 4 cm from the distal tip (end 106) and ending approximately 8 cm from the distal tip. In the distal 4 cm of the ETT 100, between the expandable cuff 107 and the distal tip of the ETT 100, there is a pair of oval holes 108, one each on the opposite surface of the tube 102 facing each other. The size of the holes 108 can vary between 5 mm and 1 cm.

A first conduit or tube 120, i.e. primary cannula, of approximately 1 mm diameter runs within the wall on the convex side of the tube(s) 102 and is connected to the expandable cuff 107 for inflation and deflation by being terminated on the outer surface of the ET tube 102 as an opening 122, such as 1 mm opening. This tube 120 alternatively can be attached on the outer surface of the tube 102 on the convex side.

The primary conduit 120 has a proximal flexible part 130 which continues outside the main tubular structure of the ETT 100 and is in fluid communication with the primary conduit 120. The flexible part 130 starts at approximately 18 cm from the distal tip of the ETT 100 and continues proximally for a few centimeters to terminate into a cuff inflation indicator 140 and adapter 142 for a syringe. The connection between the flexible and rigid part of the primary cannula or conduit 120 is through an opening 129 on the outer surface of the ETT 100 which can be about 1 mm in ID (inner diameter). On the lateral surface of the ETT 100 starting at the same level as the cannulation for the inflation of the balloon 107 or at a higher level (as shown in FIG. 1), a secondary conduit or cannula 150 is provided. A portion of the secondary conduit 150 communicates with a member that extends from the tube 102 as described below, while another portion of the conduit 150 is disposed and formed within the wall of the ETT 100. The ID of this secondary conduit 150 can vary from 0.01 mm to 1.25 mm in size.

This secondary conduit 150 continues distally beyond the balloon 107 to terminate as a pinhole opening 152 at the distal tip of the ETT 100. The course of the secondary conduit 150 within the wall of ETT 100 is preferably variable. The secondary conduit 150 is in fluid communication with an exterior, semi-flexible proximal cannula or conduit 160 which is on the outside of the main tubular structure of the ETT 100 without adhering to it just like the flexible part 130 of the primary conduit 120. The semi-flexible conduit 160 makes a connection with the secondary conduit 150 through an opening 154 on the outer surface of the ETT 100. The proximal end of the flexible cannula terminates into a metered dose inhaler (MDI) adapter 170.

The flexible conduit 160 can be an extension of MDI adapter 170 or the two can be fused together if made of different materials. A proximal port 172 of the MDI adapter 170 is designed to fit the nozzle of MDI canister (not shown). The distal end of the adapter 170 tapers into a cylindrical tube matable to the flexible conduit 160, the two made of different polymers. This assembly enables aerosolized medication from MDI canister to be delivered at the distal tip of the ETT 100 on actuation of the canister. The device may include a special syringe, the terminal injection port of which may have a configuration identical to the nozzle of the MDI. This would enable the MDI port 172 to be used for delivering any liquid medication to the respiratory system via a manually operated syringe or any pressurized source. The port 172 can include a cap for closure when not in use.

FIG. 2 shows the longitudinal view of an ETT 200 that according to an alternative embodiment illustrated additional secondary conduit features. A primary conduit 210 runs on the convex wall of the ETT 200 to terminate as an orifice 212 on the outer surface. This ETT 100 incorporates two secondary conduits 220, 230, as opposed to one shown in FIG. 1. The two points of origin of the secondary conduits 220, 230, as demonstrated in FIG. 2, are generally at the same level. The secondary conduits 220, 230 may or may not have similar tracts. The conduits 220, 230 are located on the opposite lateral surfaces of the ETT 200 and continue distally to terminate as two pinhole orifices 222, 232, respectively at the distal tip of the ETT 100. The secondary conduits 220, 230 are in fluid communication with a pair of respective semi-flexible proximal conduits (tubules) 240, 250, respectively. The flexible tubules 240, 250 can be either extensions of the MDI adapters 170 or matable with it as shown in FIG. 1. Also the length of the flexible tubule 240, 250 outside the main tubular structure of ETT 200 could be altered as can the length of secondary conduits 220, 230 in the wall of the ETT 200.

There are numerous varieties of plastic materials that may be used to manufacture the endotracheal tubes (ETT's) of the present invention; some examples of the same may be—thermoplastics (polyvinyl chloride, polyethylene, polypropylene) silicone, Teflon, etc.; though the one that is most commonly use is polyvinyl chloride (PVC). Since the differences in the compliance and coefficient of friction of various materials could influence the delivery of aerosol medication, the secondary cannulation could be coextruded using a compound or a polymer different from the one used to manufacture the primary ETT. The coextrusion may optimize the physical properties of the secondary lumen and maximize aerosol delivery. Examples of some coextrusions may be—PVC and Teflon, PVC and polypropylene, PVC and silicone, PVC and polyethylene, etc. ETT may be disposable or reusable after sterilization.

FIG. 3 is a side view of another embodiment of the present invention. The detailed description of FIG. 3 and the function and operation for this embodiment of an ETT 300 will become obvious with the explanation outlined below.

Particle Size, Plume Characteristics and Drug Delivery

Effective drug delivery is closely related to particle size. Larger particles may provide a greater total drug deliver; however, a uniform distribution of medication in the distal tracheobronchial tree requires particle size distribution in the respirable range (<5 microns). Besides particle size, the drug delivery rate and distribution is also a function of the site if aerosol particle generation and the characteristics of the aerosol plume. Even though the size of aerosol particles generated in case of a suspension of pulverized powder medication in a liquid propellant is predetermined and is a function of the size of the crushed solid particles of powder medication, the drug delivery rate and distribution will be tremendously affected by the features of secondary conduits and the terminal orifice at its tip. The critical features of secondary conduits are its length, ID, shape and orientation/trajectory. The features of the distal orifice are its location, orientation, shape, and ID. All the aforementioned features will also influence the plume geometry, velocity and orientation and hence the distribution of the particles in the distal tracheolbronchial tree.

According to the present invention, the ID of the secondary conduit may be uniform throughout or tapered along the entire length. Alternatively, it may be uniform in the proximal part and tapered near the distal part. The ID of the secondary conduit may vary from 0.01 mm to 1.25 mm. The combined length of the secondary conduit within the wall of the ETT and its proximal flexible part may also play a critical role in the total drug delivery. A narrow ID of the secondary conduit is very important for the aerosol medication to reach the distal tip of the secondary conduit over approximately 25-30 cm of length; however, if the ID is too narrow, it may pose resistance to the flow and impede aerosol delivery. Another very important factor is the course (trajectory) of the secondary conduit in the wall of the ETT. The trajectory may be directed from the outer wall to the inner wall; alternatively the secondary lumen may stay closer to the outer wall throughout; it may stay closer to the inner wall throughout; or it may stay closer to the outer wall for the most part and may be redirected to the inner wall near the distal part of the ETT. A change in the plane of the secondary conduit in the distal part of the ETT (range 1 mm-10 mm) will change the orientation of the secondary lumen by approximately 5 to 45 degrees. The preferable change in the angle, however, may be 10-15 degrees only in order to prevent tracheal or carinal impaction losses. In another modification of the present invention, the secondary conduit can run inside the primary conduit on the inner wall of the ETT or it can run on the surface on the outer wall of the ETT.

The features of the distal orifice in the present invention can also have numerous variations. The distal orifice of the secondary conduit is located at the tip of the ETT, preferably not in communication with the primary conduit at the ETT and not protruding beyond the distal tip of the ETT. The shape of the distal orifice is preferably circular, however, the shape may be semi circular, lunar, etc. The ID of the distal orifice, which may vary from 0.01 mm to 1.25 mm, may be the same or different from the ID of the secondary conduit. The ID of the distal orifice may be made extremely small to generate a narrow plume or the terminal orifice may be made larger than the secondary conduit with splaying in order to generate a wider plume. The location of the orifice may be closer to the inner wall or outer wall or it may be in the center of the ETT's wall.

An aerosol plume which is central, and wide will result in a greater fraction of the drug loss due to impaction on the ETT (if generated proximal to the ETT or in the lumen of the ETT) or the wall of the trachea (if generated distal to the ETT) prior to reaching the distal tracheobronchial tree. An aerosol plume that is central, narrow and fast is likely to lose a greater portion of the medication by carinal impaction. An eccentrically located narrow and fast plume will avoid carinal as well as tracheal impaction losses and will ensure aerosol particle delivery to the proximal tracheobronchial tree. The distal tracheobronchial tree delivery may require an eccentric, narrow and slower plume or an eccentric wide and fast plume.

In the present invention, the distal orifice of the secondary conduit is located at the tip of the ETT and generates aerosol at a location in the tracheobronchial tree beyond the ETT, thus avoiding impaction losses. The velocity and width of the plume could be altered by adjusting the shape and ID of the secondary conduit and the distal orifice. Over and above the orientation of the plume can be influenced by the trajectory of the secondary conduit. In our invention, since the trajectory is from the outer wall towards the inner wall, preferably in the distal part of the secondary conduit, the plume will be oriented away from the tracheal wall. The eccentric location of the orifice in the wall of the ETT in our invention is preferable as it prevents carinal and tracheal impaction losses. The diameter of the ETT is far smaller than that of the airway passages i.e., the trachea. On placement of the ETT in the trachea and inflating the distal balloon, the wall of the distal circular edge of the ETT is a few millimeters away from the tracheal wall and hence the orifice located in the wall of the distal tip of ETT. Depending on the size of the ETT the two lateral terminal orifices of secondary conduits may be located approximately in the center between the carina and the left or right mainstem bronchi.

One may argue that the lateral location of the orifice would direct the plume preferentially to one lung. This actually may be of tremendous benefit if one wants preferential delivery of medication to one lung which has the pathology. However, if the pathological condition affects both the lungs uniformly the problem can be completely obviated by having two distal orifices diametrically opposite to each other on the lateral surface of the ETT as described in the second embodiment of the present invention in FIG. 2. It is also quite conceivable that at the time of placement of the ETT and inflation of the balloon, the ETT may get slightly rotated so that the two lateral orifices may not end up being in the preferred 3 o'clock and 9 o'clock positions. This problem of misalignment of the two lateral orifices with respect to the carina and the right and/or left mainstem bronchi can be overcome by the most preferable embodiment of our invention as described in FIG. 3.

FIG. 3 shows the longitudinal view of the ETT 300 associated with an alternative embodiment of secondary conduit. FIG. 3 demonstrates an embodiment of the present invention with six secondary conduits or cannulations 302 in a wall 301 of the ETT 300 terminating in six distal orifices 310 located on the circular edge of a distal tip 312 of the ETT 300. The six orifices 310 may preferably be equidistant from each other like the six edges of a hexagon at 1, 3, 5, 7, 9 and 11 o'clock positions. However, the six orifices 310 may have several alternative symmetric or asymmetric arrangements. The six secondary conduits 302 and their distal orifices 310 may be identical or completely different from each other in shape, ID, trajectory, and orientation. Such an arrangement would generate plumes with different characteristics i.e. geometry, velocity and orientation. In this respect, a preferable arrangement would be to have three orifices on each lateral surface of the ETT 300 with the ability to generate narrow and fast, narrow and slow, and wide and fast plumes from the three orifices on each side. In another arrangement, there could be eight secondary conduits and orifices, four each on the two lateral surfaces in order to generate the wide and slow eccentric plume as well. This arrangement with total eight plumes (3/4 plumes with different characteristics and orientation on each lateral surface) will ensure a uniform and effective distribution of aerosol particles to proximal and distal tracheobronchial tree of both lungs.

FIG. 3 shows the longitudinal view of the ETT 300, an adapter at its proximal end 320 and an inflation cuff 322. A primary conduit 330 has a flexible portion 332, a point of origin 334 of the primary conduit 330, distal orifice 336 and proximal cuff inflation indicating an adapter for syringe 340. There are six secondary conduits 302 in the wall of the ETT 300. They originate on the outer surface of the ETT 300 at the same level at the point of origin 334 or a level higher than the primary conduit 330. The six conduits 302 continue distally in the wall of the ETT 300 to terminate as six orifices, as described before, at the distal tip of the ETT 300. Two out of six secondary conduits 302 and a single distal orifice 310 of the secondary conduit 302 are demonstrated in FIG. 3. The secondary conduit continue proximally as six semiflexible tubules 350 outside the main tubular structure of the ETT 300 without adhering to it just like the flexible part 332 of primary conduit 330. The six flexible tubules are packaged in a larger hollow tube 360 that terminates distally on the outer wall of the ETT 300. This arrangement however may be changed and there could be two larger hollow tubes packaging three flexible tubules on each side. The proximal end of the hollow tube 360 and the six tubules 350 terminate on the under surface of a circular plate 370. The six flexible tubules 350 terminate as six MDI adapters, or alternatively, the six tubules 350 terminate as six rigid cylindrical tubules for mating with MDI adapters on the ventral surface of the circular plate 370. The circular plate 370 is attached to another circular plate through a central connector 380. The central connector 380 has a circular groove in the center and six grooves perpendicular to the circular grooves that are in alignment (parallel) with the six MDI adapters. The lower circular plate 370 is fixed to the central connector 380 whereas an upper circular plate 372 can rotate around the circular groove as well as move up and down along the perpendicular grooves of the central connector with the help of a handle 374. Located on the peripheral rim of the ventral surface of the upper plate 372 is an MDI adapter 382. The nozzle of a pressurized canister fits into the proximal port of MDI adapter 382. The MDI adapter 382 tapers distally to terminate on the undersurface of the upper circular plate 372. The MDI adapter 382 locks into one of the rigid cylindrical tubules, the proximal end of the flexible tubules 350, located on the dorsal surface of the lower plate. The upper circular plate 372 can rotate in the circular groove, move superiorly along the perpendicular groove (to unlock) and move inferiorly along the perpendicular groove (to lock) the MDI adapter into six rigid cylindrical tubules one at a time in six different positions. Hence, actuation of MDI in different positions would result in generation of six aerosol plumes at the distal orifices 310 of the secondary cannulations 302.

FIG. 4 shows an alternative embodiment of our invention to further obviate the tracheal deposition of aerosol particles as well as alter the aerosol particle size. FIG. 4, which shows the longitudinal view of an ETT 400, is identical to the ETT 300 described in FIG. 3 but has two alternative features. Six flexible conduits (tubules) 402 and six secondary conduits 404 in the wall of the ETT 400 have two coaxial lumens. The secondary conduits 404 terminate as two coaxial orifices 406 at the distal tip of the ETT 400. The flexible conduits 402 are packaged in a hollow tube 410, the proximal end of which terminates on the dorsal end of a lower circular plate 412 along with the flexible tubules 402. The distal end terminates on the outer wall of the ETT 400. A point of entry or fusion 403 represents the joining or mating of the secondary conduits 404 with the six flexible tubules 402 on the wall of the ETT 400 and is illustrated in FIG. 4. Primary cannulations 420 with all the associated features, including, distal tip 422, inflatable cuff 424, flexible cannula 426, entry point 428 and cuff inflation indicator and adapter 430 are also demonstrated in FIG. 4.

According to a second alternative embodiment, a modified MDI adapter 440 with an additional side port 442. The upper circular plate 444, with a handle 446, along with a central connector 448 are demonstrated. The MDI adapter has two ports. The main port 440 that has a proximal port to fit the nozzle of the pressurized canister and a distal orifice that makes an airtight connection with the inner coaxial lumen of the rigid cylindrical tubule. It also has a side port 442 that communicates with the outer coaxial lumen of the rigid cylindrical tubule. Note that the rigid cylindrical tubule is the proximal end of the flexible tubule for mating with MDI adapter. The inner lumen of the main port of MDI adapter serves to generate aerosol particles by MDI canister or deliver liquid medication via a syringe at the distal tip of the ETT. The side port or the outer lumen of MDI adapter may be used for vapor or gas flow for either anesthesia or to disperse the aerosolized particles generated near the distal tip of ETT away from the trachea as well as to break the particle into smaller size. This device, just like the one described in FIG. 3, incorporates the special feature of MDI adapter's ability to rotate and lock in six different positions, such that through the inner coaxial lumen liquid medication or aerosol spray is conveyed and the pressurized gas is conveyed in the annular region between the inner and the outer tubular membranes. This coaxial airflow may direct the plume away from the tracheal wall and carina and hence prevent impaction losses.

A variety of drug delivery rates and particle size distribution can be achieved by altering the coaxial orifice, diameters, pressure and flow characteristics of the liquid and gas in the respective orifices and by adjusting the distance between the liquid and gas flow by altering the thickness of the membrane separating the two lumens. The liquid lumen, the gas lumen and the thickness of the wall separating the two lumens may vary from 0.025 mm to 1 mm.

In another alternative embodiment of our invention, as described in FIG. 3, there is only one circular plate without a central connector or the upper circular plate. The six flexible tubules 350 terminate into the single circular plate as six MDI adapters on the ventral surface of the plate. They may appear just like the MDI adapter demonstrated in FIG. 1. The nozzle of the MDI canister can fit into the proximal ports of MDI adapters one at a time in six different positions by manual operation. The circular plate may have a cap to cover MDI adapters when not in use.

In another alternative embodiment of our invention as described in FIG. 4, the inner coaxial lumen of the six flexible tubules 402 may terminate on the ventral surface of the circular plate 412 as MDI adapters and the outer coaxial lumen of the flexible tubules may terminate as six side ports on the outer surface of the circular edge of the single plate. In another alternative embodiment of our invention, the coaxial arrangement may be uniform and cylindrical for the most part but the inner and/or outer conduit may become semicircular in the terminal part of the ETT. The flow of gas and liquid aerosol in this arrangement would direct the aerosol plume further away from the tracheal wall. In yet another alternative embodiment of the present invention, the inner conduit may terminate just proximal to the distal tip of the outer semicircular conduit.

Figure 5A:
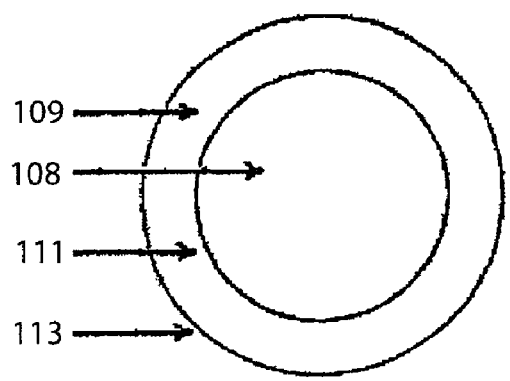
Figure 5B:
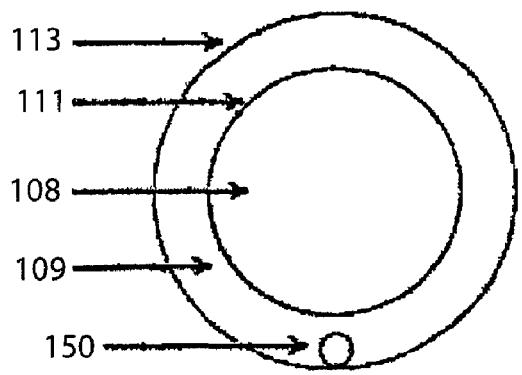
Figure 5C:
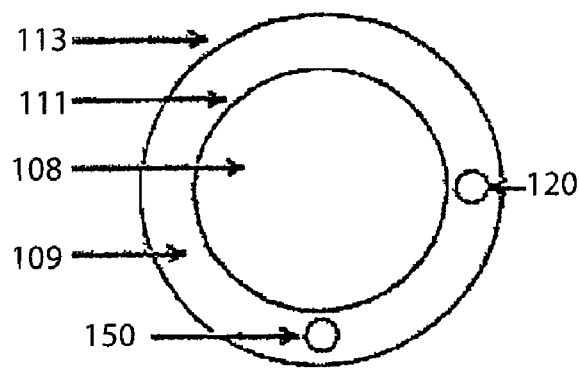
Figure 5D:
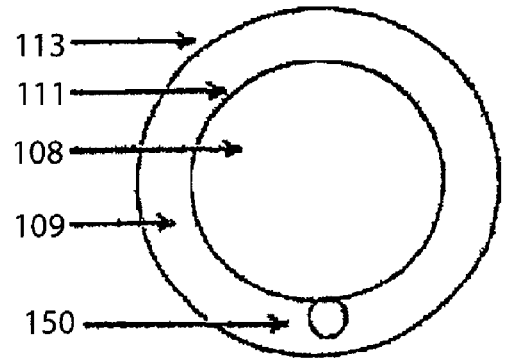
Figure 6A:
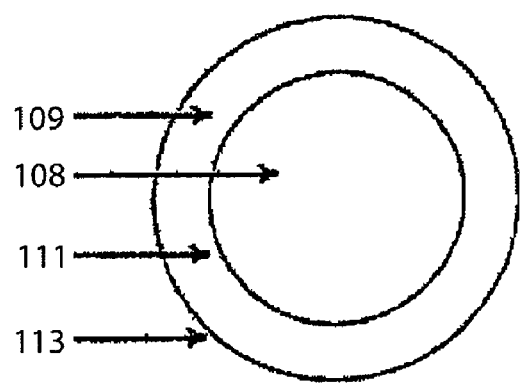
Figure 6B:
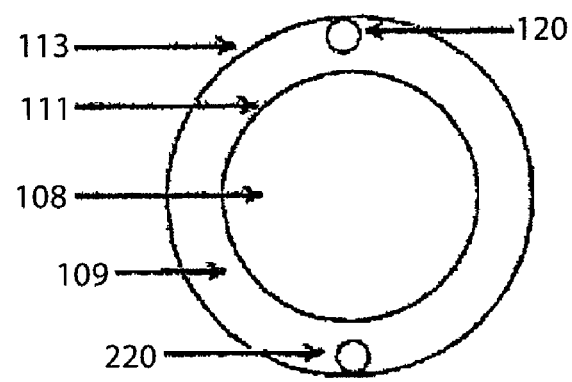
Figure 6C:
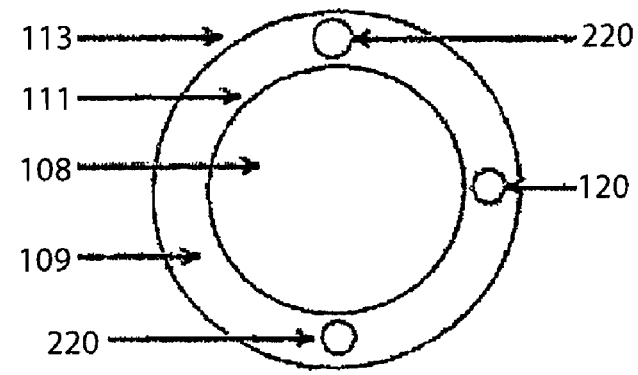
Figure 6D:
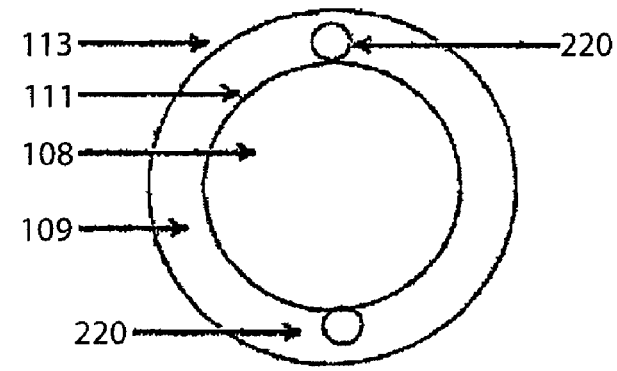

FIG. 5*a* is a cross section at level a-a of FIG. 1, which shows a hollow tube 108 with a lumen (opening), a wall 109 of the tube 108, an inner surface 111 of the wall 109, and an outer surface 113 of the wall 109.

FIG. 5*b* is a cross section at level b-b of FIG. 1 with the appearance of one additional secondary conduit 150 starting close to the outer surface 113. The main wall 109, the inner surface 111, and the lumen 108 are demonstrated.

FIG. 5*c* is the cross section at the level c-c of FIG. 1. This view is similar to FIG. 5*b*; however, the position of the secondary conduit 150 within the wall 109 has been changed in that in this Figure, the conduit 150 is moved closer to a center of the wall 109 and thus closer to the inner wall 111 of the ETT 100. The primary conduit 120 on the convex side of the ETT near the outer wall for inflation and deflation of the balloon cuff 107 is illustrated.

FIG. 5*d* is the same as FIG. 5*c* but with the absence of the primary conduit 120 as it terminates at a higher level near the expandable balloon. In this embodiment, the secondary cannula 150 is closer to the inner wall 111.

FIG. 6*a* is the same as FIG. 5*a* but for the ETT 200 and is therefore taken along the line a-a of FIG. 2.

FIG. 6*b* is the same as FIG. 5*b* but taken along the line b-b of FIG. 2, with the two secondary conduits 220 on lateral surface of the ETT 200 diametrically opposite to each other.

FIG. 6*c* is the same as FIG. 6*b* but with one primary conduit 210 as taken along the line c-c of FIG. 2.

FIG. 6*d* is the same as FIG. 6*c*, but taken along the line d-d of FIG. 2, with two secondary conduits 220 on the lateral surface near the inner wall of the ETT 200 but without the primary conduit 210.

FIGS. 7*a*, 7*b*, 7*c*, and 7*d* show the details of four cross sections at four levels, a-a, b-b, c-c, d-d, respectively, of the ETT 300 as shown in FIG. 3.

FIG. 7*a* is the same as FIG. 6*a* but for the ETT 300.

FIG. 7*b* demonstrates a main lumen 301, a wall 303 of the ETT 300, an inner wall 303, and an outer wall 305.

There is appearance of six secondary conduits 320 which enter the ETT 320 approximately at the same level but follow different tracts in the wall of the ETT 300.

FIG. 7*c* is the same as FIG. 7*b* but with one additional primary conduit. The six secondary conduits 320; however, are most separated as they follow different tracts within the wall of the ETT 300.

FIG. 7*d* is the same as FIG. 7*c* but with disappearance of primary conduit 330. The six secondary conduits 320 now appear as the six edges of a hexagon on the distal tip close to the inner wall of the ETT 300. The six distal orifices 310 may not be equidistant from each other and may be have alternative arrangement along the circular edge of the tip of the ETT 300.

FIGS. 8*a*, 8*b*, 8*c*, and 8*d* show details of four cross sections at four levels a-a, b-b, c-c, and d-d, respectively, with respect to the alternative embodiment as shown in FIG. 4. A main lumen 431, a wall 433 of the ETT 400 that includes inner wall 437 and outer wall 439 are illustrated.

FIGS. 8*a*, 8*b*, 8*c*, and 8*d* are the same as the embodiments of FIGS. 7*a*, 7*b*, 7*c*, and 7*d* respectively; with the only difference being that the secondary conduits 404 of FIGS. 8*a*-8*d* have two coaxial lumens as opposed to a single lumen as shown in FIG. 7.

FIGS. 9*a*, 9*b*, 9*c*, and 9*d* represent another alternative embodiment of the needle 400 of FIG. 4. FIGS. 9*a*, 9*b*, and 9*c* are identical to FIGS. 8*a*, 8*b*, and 8*c*. FIG. 9*d* is the same as FIG. 8*d* except for a single modification. The two coaxial secondary conduits 404 in 9*d* are different from the ones in FIG. 8*d*. FIG. 9*d* has circular inner lumen 431 just as demonstrated in FIG. 8*d* but the outer coaxial lumen is semi-circular as opposed to circular as demonstrated in FIG. 8*d*. Alternatively, in another embodiment both inner and outer lumen in 9*d* can be semi-circular with the circular edges on the opposite lateral sides.

FIG. 10 shows details of a cross sectional view of the lower circular plate 412, the six flexible tubules 402 are formed at or near the ventral surface of the peripheral rim of the circular plate 412 like the six edges of a hexagon. The central connector 448, along with the central attachment, is also demonstrated here.

FIG. 11 shows the details of a cross-sectional view of another embodiment of the lower circular plate 412 that corresponds to the embodiment of FIG. 4. This is similar to FIG. 10, but with a single modification, namely, that the six tubules 402 have two coaxial lumens, an inner one 403 for the liquid medication or liquid aerosol, and an outer one 405 for the gas or vapor flow. The circular plate 412, the flexible tubules 402, the peripheral rim of the circular plate 412, the central connector 448, and the central attachment of the plate 412 to a rod 419 are demonstrated.

FIG. 12 is a partial perspective view of the lower circular plate 412. Each of the flexible tubule 402 terminates as rigid cylindrical tubule on the ventral surface of the peripheral rim of the circular plate 412.

FIG. 13 is a partial perspective view of the lower circular plate 412 shown in FIG. 11. The two coaxial tubules—inner 403 and outer 405 terminate on the ventral surface of the circular plate 412.

FIG. 14 shows MDI adapter 170 as shown in FIGS. 1 and 2. The MDI adapter 170 is located in the center at a circular plate 171 with peripheral handles 173, 175. The MDI adapter 170 tapers distally to continue as a single flexible tubule 177 that extends as secondary conduit (not shown) in the wall of the ETT.

FIG. 15 shows the upper plate with MDI adapter 382, as shown in FIG. 3. A single MDI adapter 382 on the peripheral rim of the circular plate 372 is demonstrated here. The circular plate 372 rotates around the central connector 380 in a central groove 383. To facilitate the rotation, the central plate has the handle 374.

FIG. 16 shows upper plate 444 with MDI adapter 420 with the handle 446, a central connector and attachment 448 as shown in FIG. 4. A single MDI adapter 440 with a side port 442 is attached to the circular plate 444 at its peripheral rim.

FIG. 17 shows the top cross sectional view of MDI adapter shown in FIGS. 14, 15, and 16. The MDI adapter has an inlet port 500 and two concentric rings 502, 504 with decreasing circumferential perimeter such that the MDI nozzle locks into the innermost concentric ring 504. The terminal orifice 506 marks the point of fusion or mating with the proximal end of the flexible tubule. The structure of the internal lumen of MDI adapter could be modified in numerous ways to fit the nozzle of the MDI.

FIG. 18 shows the bottom cross sectional view of the MDI adapter shown in FIGS. 14 and 15. The MDI adapter's innermost ring to fit the nozzle of MDI and the distal orifice 509 through which the aerosol particles are generated are demonstrated in this figure.

FIG. 19 shows the bottom cross sectional view of the MDI adapter shown in FIG. 16. It is the same as FIG. 18 except for one extra outer ring 510. The shaded area 512 between the two rings 510, 514 is a tubular hollow space that communicates with a side port 442 shown in FIG. 16. This hollow space is the coaxial outer lumen.

FIG. 20 shows the upper and the lower plates together as shown in FIGS. 3, 12 and 15.

FIG. 21 shows the upper and the lower plates together as shown in FIGS. 4, 13 and 16.

FIG. 22 demonstrates an alternative embodiment of FIG. 21 with the upper and lower plates aligned together. As opposed to the MDI adapter having a side port for the gas flow, the side port 520 could be a part of the assembly of the lower plate 412. The central flexible tubule 402 terminates proximally on the ventral surface 522 of the lower plate 412. The side port 520 terminates proximally on the dorsal surface of the lower plate 412. Distally the side port continues as the outer coaxial flexible tubule 405. The MDI adapter 440 of the upper plate locks into the proximal orifice of the flexible tubule 402. The MDI adapter 440 can lock in six different positions one at a time with each of the flexible tubules as described earlier. The side port 520 serves the purpose of gas or vapor flow to the outer coaxial lumen.

Figure 7A:
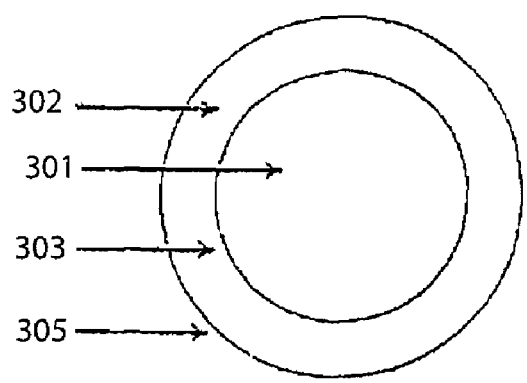
Figure 7B:
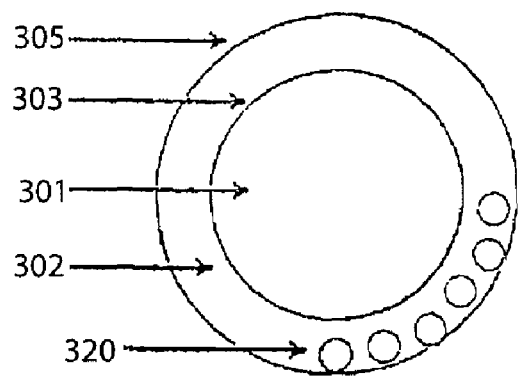
Figure 7C:
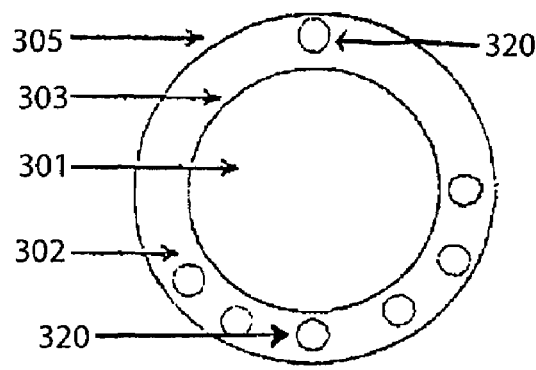
Figure 7D:
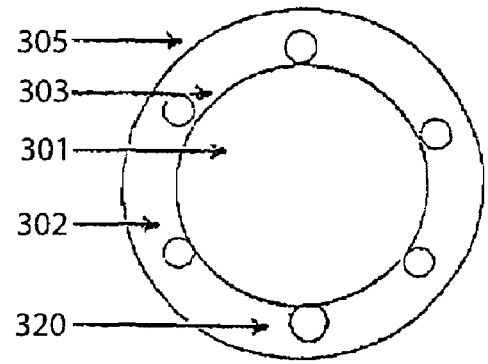

FIG. 23 shows the cross sectional view of the ETT as shown in FIG. 7d along with two dimensional geometry and direction of the plume generated from each of the orifices of secondary cannulations at the distal tip of the ETT. The terminal orifice generates a plume that moves distally along the inner circular edge of the ETT (arrows 530 and 532) as well as away from the inner edge (arrow 534). The area under the curve of the aerosol plume generated from any one orifice maybe approximately ⅓ to ½ of the area formed by the primary lumen 301 at the endotracheal tube 300. The six aerosol plumes generated from six distal orifices ensure uniform distribution of medication in the tracheobroncial tree of both lungs as demonstrated.

Figure 8A:
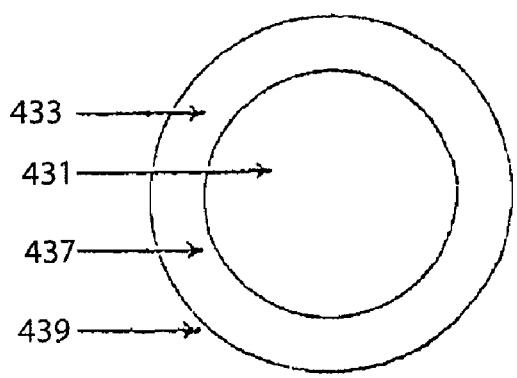
Figure 8B:
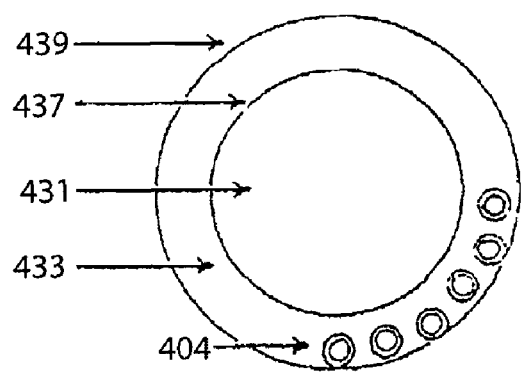
Figure 8C:
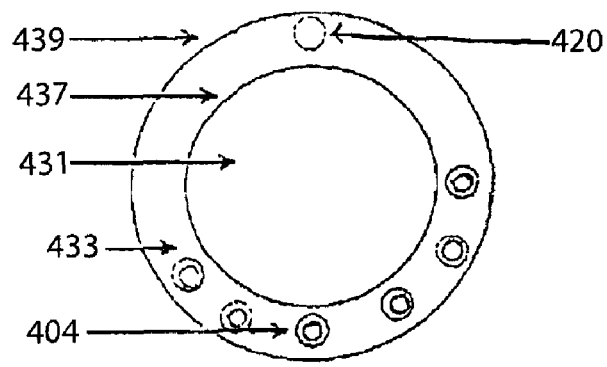
Figure 8D:
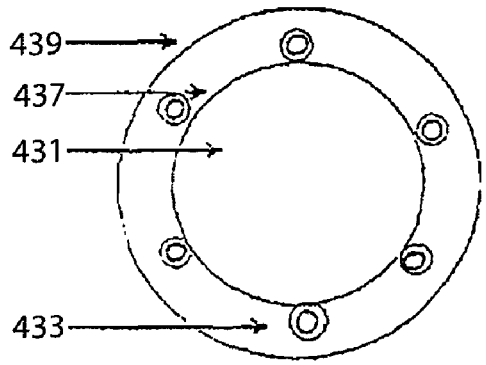

FIG. 24 is the same as FIG. 8d with the direction of the plumes as shown in FIG. 23. The airflow in the outer coaxial tube will prevent the tracheal and carinal impaction of aerosol particles.

FIG. 25 is the same as FIG. 9d with the direction of the plume being further away from the tracheal wall 433. In this figure the airflow from the semi-circular outer coaxial tube 405 will redirect the liquid aerosol from the inner lumen 403 away from the tracheal wall.

It is noted that the illustration (drawings) and description of the preferred embodiments have been provided merely for the purpose of explanation and although the invention has been described herein with reference to particular means, materials and embodiments, the invention is not intended to be limited to the particulars disclosed herein; rather the invention intends to all functionally equivalent structures, methods and uses such as are within the scope of the appended claims.

What is claimed is:

1. An endotracheal tube for insertion into a patient's trachea and including a drug delivery feature comprising:
    an elongated body having a proximal end for connection to a ventilator device and an opposing distal end with a bore formed therein and terminating in at least one ventilation opening; and
    a plurality of drug delivery conduits formed in the elongated body and radially about the bore within the elongated body and each terminating at one end with a proximal opening and at an opposite end with a distal opening, the proximal opening being adapted to be fluidly connected to a drug delivery device adapter, each drug delivery conduit being fluidly separated from the bore, wherein each of the drug delivery conduits comprises a pair of coaxial lumens, namely an inner coaxial lumen and an outer coaxial lumen and as a result, the distal opening is defined by a pair of co-axial orifices;

wherein each drug delivery conduit is separated from the bore along its entire length thereof from the proximal opening to the distal opening, the distal opening being formed at the distal end of the elongated body and is located closer to the distal end than the ventilation opening, wherein each of the plurality of drug delivery conduits is fluidly connected to a different flexible external conduit member that is external to the elongated body and is fluidly connected to the proximal opening of the drug delivery conduit at a first end and terminates at a second end as one drug delivery adapter, the flexible external conduit members being bundled together in a manner that maintains their separation from one another and wherein each of the drug delivery adapters mates with a single main connector that is in selective communication with an MDI adapter that is adapted for attachment to an MDI device, the main connector and the MDI adapter being remote from the elongated tube and only attached thereto by means of the flexible external conduit members, the main connector and MDI adapter being located at free ends of the flexible external conduit members remote from the elongated tube, the MDI adapter having a main port with a first end for attachment to the MDI device for receiving already aerosolized medication and an opposite second end that forms an airtight connection with the inner coaxial lumen, the MDI adapter having a side port that fluidly communicates with the outer coaxial lumen to permit a supplemental pressurized gas to flow through the outer coaxial lumen to the distal opening, the main connector having a component that is rotatable so as to place the MDI adapter in fluid communication with one of the external conduit members associated with one drug delivery conduit to permit delivery of medication along one drug delivery path defined by the selected external conduit member, while maintaining flow of the aerosolized medication into the inner coaxial lumen and the supplemental pressurized gas into the outer coaxial lumen.

2. The endotracheal tube of claim 1, further including:
    an expandable member formed about the elongated tube near the distal end thereof;
    a primary conduit formed in the elongated body and terminating in a first orifice that is in fluid communication with the expandable member for inflating the expandable member, the primary conduit terminating at an opposite end in a second orifice which is suitable for connection to an inflation adapter for causing inflation of the expandable member.

3. The endotracheal tube of claim 2, further including:
    a first flexible external conduit member that is external to the elongated body and is fluidly connected to the second orifice at a first end thereof end and is in fluid communication at a second end with the inflation adapter.

4. The endotracheal tube of claim 1, wherein the drug delivery conduit has a variable diameter along its length from the proximal opening to the distal opening.

5. The endotracheal tube of claim 4, wherein a diameter of the drug delivery conduit near the proximal opening is greater than a diameter of the drug delivery conduit at the distal opening.

6. The endotracheal tube of claim 4, wherein the drug delivery conduit has a trajectory as measured relative to an inner wall and an outer wall of the elongated body, the trajectory of the drug delivery device being different in a first region near the proximal opening compared to a second region near the distal opening.

7. The endotracheal tube of claim 6, wherein the drug delivery conduit is formed closer to the outer wall in the first region compared to the second region where the drug delivery conduit is formed closer to the inner wall.

8. The endotracheal tube of claim 6, wherein the trajectory is such that an angle is defined between a plane extending along a substantial length of the drug delivery conduit and a reference plane that contains the outer wall of the elongated body, the angle being selected to produce a desired plume trajectory.

9. The endotracheal tube of claim 1, wherein the ventilation opening is formed in a side wall of the elongated body and is spaced from a distalmost tip of the elongated body.

10. The endotracheal tube of claim 9, wherein the angle is between approximately 5 and 45 degrees.

11. The endotracheal tube of claim 1, wherein the at least one ventilation opening comprises two or more ventilation openings each formed in the side walls on opposite faces thereof.

12. The endotracheal tube of claim 1, wherein the distal opening is formed in the elongated body such that drug is discharged from the distal opening at a location that is more distal compared to the location where gas is discharged from the ventilation opening.

13. The endotracheal tube of claim 1, wherein the distal opening is closer to the distal end than the inflatable member.

14. The endotracheal tube of claim 1, wherein the main connector includes a first plate, a second plate, and a central connector disposed between the first and second plates, with the central connector serving to connect the first plate to the second plate, each of the drug delivery adapters being formed as part of the first plate, the central connector having a central groove and a plurality of secondary grooves perpendicular to the central groove and parallel to the drug delivery adapter.

15. The endotracheal tube of claim 14, wherein the first plate is fixed to the central connector, while the second plate is rotatable relative to the central connector and about the central groove as well as move up and down along the perpendicular secondary grooves.

16. The endotracheal tube of claim 15, wherein the MDI adapter is located on one face of the second plate, the MDI adapter tapering distally to terminate on an underside surface of the second plate, wherein rotation of the second plate relative to the central connector causes the MDI adapter to align and lock into place relative to one of the drug delivery adapters for providing a fluid path between a drug delivery device and one of the drug delivery conduits.

17. The endotracheal tube of claim 15, wherein the second plate can rotate in the central groove, move superiorly along the perpendicular groove to unlock the MDI adapter from one of the drug delivery conduits, and move inferiorly along the perpendicular groove to lock the MDI adapter into one of the drug delivery conduits.

18. The endotracheal tube of claim 1, wherein the plurality of flexible external conduit member are disposed within a single sheath member.

19. The endotracheal tube of claim 1, wherein one of the coaxial lumens has a circular cross-section, while the other of the coaxial lumens has a different second cross-section.

20. A drug delivery system comprising:
an MDI device for delivering aerosolized medication;
an endotracheal tube for insertion into a patient's trachea comprising:
an elongated body having a proximal end for connection to a ventilator device and an opposing distal end with a bore formed therein and terminating in at least one ventilation opening; and
a plurality of rigid drug delivery conduits formed in the elongated body and terminating at one end with a proximal opening and at an opposite end with a distal opening, the proximal opening;
wherein each drug delivery conduit is separated from the bore along its entire length thereof from the proximal opening to the distal opening, the distal opening being formed at the distal end of the elongated body and is located closer to the distal end than the ventilation opening;
a plurality of flexible external drug delivery conduits each of which is external to the elongated body and is fluidly connected to the proximal opening of the drug delivery conduit at a first end and terminates at a second end as one drug delivery adapter; and
a positionable MDI adapter assembly for selectively fluidly linking one of the drug delivery conduits with the MDI device so that actuation of the MDI device results in the aerosolized medication being delivered through the one drug delivery conduit to the distal opening, the MDI adapter assembly being movable between a plurality of positions wherein in each position, the MDI is fluidly linked to one of the external conduit members that is associated with one drug delivery conduit, the MDI adapter assembly including a nozzle that is received in the selected drug delivery adapter, the adapter assembly including a main connector that includes a first plate, a second plate, and a central connector disposed between the first and second plates, with the central connector serving to connect the first plate to the second plate, each of the drug delivery adapters being formed as part of the first plate;
wherein each of the flexible external drug delivery conduit and the rigid drug delivery conduit is defined by an inner conduit member and an outer conduit member that is co-axial to and surrounds the inner conduit member, the inner conduit member being integrally coupled to the first plate such that it is fluidly connected to the MDI device and receives medication that is already in an aerosolized state, the outer conduit member being formed below the first plate and includes an integral side port that extends outwardly from the elongated body that permits gas flow within the outer conduit member, the side port being connected to a pressurized gas source that flows within the outer conduit member to the distal opening;
wherein at least two or more of the drug delivery conduits produce aerosol plumes of the medication that have different plume characteristics compared to one another based on a trajectory of each drug delivery conduit in the elongated body and an orientation of each distal opening, the coaxial flow of aerosolized medication and the pressurized gas serving to direct the plume away from a tracheal wall and carina of the patient, thereby preventing impaction losses.

21. The system of claim 20, wherein the distal opening is formed in the elongated body such that drug is discharged from the distal opening at a location that is more distal compared to the location where gas is discharged from the ventilation opening.

* * * * *